United States Patent [19]

Suresh et al.

[11] Patent Number: 5,093,299
[45] Date of Patent: Mar. 3, 1992

[54] CATALYST FOR PROCESS FOR THE MANUFACTURE OF ACRYLONITRILE AND METHACRYLONITRILE

[75] Inventors: Dev D. Suresh, Hudson; Maria S. Friedrich, Lyndhurst; Michael J. Seely, Twinsburg, all of Ohio

[73] Assignee: The Standard Oil Company, Cleveland, Ohio

[21] Appl. No.: 462,202

[22] Filed: Jan. 9, 1990

[51] Int. Cl.$^5$ .................. B01J 23/78; B01J 23/84; B01J 23/88; B01J 27/185
[52] U.S. Cl. .................. 502/212; 502/215; 502/241; 502/243; 502/304; 502/306
[58] Field of Search ............ 502/212, 215, 241, 243, 502/304, 306

[56] References Cited

U.S. PATENT DOCUMENTS

| | | | |
|---|---|---|---|
| 3,230,246 | 1/1966 | Callahan et al. | 260/465.3 |
| 3,642,930 | 2/1972 | Grasselli et al. | 260/680 |
| 4,503,001 | 3/1985 | Grasselli et al. | 260/465.3 |
| 4,767,878 | 8/1988 | Grasselli et al. | 558/324 |
| 4,863,891 | 9/1989 | Grasselli et al. | 502/306 |

Primary Examiner—W. J. Shine
Attorney, Agent, or Firm—Larry W. Evans; Michael F. Esposito; Scott A. McCollister

[57] ABSTRACT

Olefins such as propylene and isobutylene are converted to the corresponding unsaturated nitriles, acrylonitrile, and methacrylonitrile, respectively, by reacting a mixture of the olefin, ammonia, and molecular oxygen-containing gas in the presence of a catalyst containing the oxides of bismuth, molybdenum, iron, nickel and magnesium, at least one element selected from the group comprising potassium and cesium, and optionally one element selected from the group comprising cobalt, phosphorus, manganese, tellurium, sodium, cerium, chromium, antimony and tungsten wherein the sum of cesium and potassium is at least 0.1 to 0.4.

4 Claims, No Drawings

CATALYST FOR PROCESS FOR THE MANUFACTURE OF ACRYLONITRILE AND METHACRYLONITRILE

BACKGROUND OF THE INVENTION

This invention relates to an improved process and catalyst for the ammoxidation of olefin-ammonia mixtures to unsaturated nitriles, and more particularly to an improved process and catalyst for the ammoxidation of propylene-ammonia and isobutylene-ammonia to acrylonitrile and methacrylonitrile, respectively. The ammoxidation is conducted in the presence of a catalyst comprising at least one element selected from the group comprising potassium and cesium, and the oxides of bismuth, molybdenum, iron, nickel, and magnesium, and optionally in combination with at least one element selected from the group of cobalt, phosphorus, manganese, tellurium, sodium, cerium, chromium, antimony and tungsten.

There are many patents related to the production of acrylonitrile by use of bismuth-molybdenum-iron fluidized bed catalyst (e.g., 3,642,930). In particular, U.S. Pat. No. 4,863,891, issued Sept. 5, 1989, and U.S. Pat. No. 4,767,878, issued Aug. 30, 1988, disclose a process for acrylonitrile production using a catalyst comprised of the oxides bismuth, molybdenum, iron, magnesium and optionally the oxides of cobalt, nickel, phosphorous, arsenic and an alkali metal present in an amount less than 0.1.

The catalyst employed in the process of this invention has high activity for the production of unsaturated nitriles at a slightly lower reaction temperature than is normally employed for this type of process, and continues efficient low temperature operation after aging. In addition to high activity for nitrile production, the catalyst has a number of other important advantages that contribute greatly to the efficient and economic operation of the process. The catalyst has excellent redox stability under the reaction conditions of the process. This permits the use of low process air to olefin ratios and high weight hourly space velocities. The catalyst exhibits efficient ammonia utilization thus greatly reducing the amount of unreacted ammonia appearing in the reactor effluent and thus lowering the amount of sulfuric acid required to neutralize the ammonia in the effluent. This results in improvements in (1) the operation of the recovery section of the process and (2) pollution control. The use of lower operating temperatures favors longer catalyst life and minimizes effluent problems such as afterburning. Despite the lower reaction temperatures, per pass conversions to the nitrile product of 84 percent and above are obtained. A further important advantage associated with the catalyst of this invention is the low cost of the essential catalytic components and the ease of catalyst preparation.

The reactants employed in producing the unsaturated nitriles of this invention are oxygen, ammonia, and an olefin having three carbon atoms in a straight chain such as propylene or isobutylene, and mixtures thereof.

The olefins may be in a mixture with paraffinic hydrocarbons, such as ethane, propane, butane and pentane; for example, a propylene-propane mixture may constitute the feed. This makes it possible to use ordinary refinery streams without special separation. Likewise, diluents such as nitrogen and oxides of carbon may be present in the reaction mixture without deleterious effect.

In its preferred aspect, the process comprises contacting a mixture comprising propylene or isobutylene, ammonia and oxygen with the catalyst at an elevated temperature and at atmospheric or near atmospheric pressure to produce acrylonitrile or methacrylonitrile. Most preferably, the process is directed to contacting propylene, ammonia and oxygen with a fluid bed catalyst at an elevated temperature to produce acrylonitrile.

Any sources of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 4:1 and a ratio of about 1:1 to 3:1 is preferred.

The molar ratio of ammonia to olefin in the feed to the reaction may vary between about 0.5:1 to 5:1. There is no real upper limit for the ammonia-olefin ratio, but there is generally no reason to exceed a ratio of 5:1. At ammonia-olefin ratios appreciably less than the stoichiometric ratio of 1:1, various amounts of oxygenated derivates of the olefin will be formed. Outside the upper limit of this range only insignificant amounts of aldehydes and acids will be produced, and only very small amounts of nitriles will be produced at ammonia-olefin ratios below the lower limit of this range. It is surprising that within the ammonia-olefin range stated, maximum utilization of ammonia is obtained, and this is highly desirable. It is generally possible to recycle any unreacted olefin and unconverted ammonia.

We have found that in some cases water in the mixture fed to the reaction vessel improves the selectivity of the reaction and yield of nitrile. However, addition of water to the feed is not essential in this invention, inasmuch as water is formed in the course of the reaction.

In general, the molar ratio of added water to olefin, when water is added, is above about 0.25:1. Ratios on the order of 1:1 to 4:1 are particularly desirable, but higher ratios may be employed, i.e., up to about 10:1.

The reaction is carried out at a temperature within the range of from about 260° to about 600° C. The preferred temperature range is from about 310° to 500° C., especially preferred being from about 315° to 480° C.

The pressure at which the reaction is conducted is another variable, and the reaction is preferably carried out at about atmospheric or above atmospheric (2 to 5 atmospheres) pressure.

The apparent contact time is not critical, and contact times in the range of from 0.1 to about 50 seconds may be employed. The optimum contact time will, of course, vary depending upon the olefin being reacted, but in general, a contact time of from 1 to 15 seconds is preferred.

Generally any apparatus of the type suitable for carrying out oxidation/ammoxidation reactions in the vapor phase may be employed in the execution of this process. The process may be conducted either continuously or intermittently. The catalyst bed may be a fixed-bed employing a large particulate or pelleted catalyst or preferably, a so-called "fluidized" bed of catalyst may be employed. Any conventional fluid ammoxidation reactor may be utilized in the practice of the process of the present invention. For example, the reactor described in U.S. Pat. No. 3,230,246, issued Jan. 18, 1966 incorporated herein by reference would be suitable in the practice of the present invention.

The reactor may be brought to the reaction temperature before or after the introduction of the reaction feed mixture. However, in a large scale operation it is preferred to carry out the process in a continuous manner, and in such a system the circulation of the unreacted olefin is contemplated. Periodic regeneration or reactivation of the catalyst is also contemplated, and this may be accomplished, for example, by contacting the catalyst with air at an elevated temperature.

The products of the reaction may be recovered by any of the methods known to those skilled in the art. One such method involves scrubbing the effluent gases from the reactor with cold water or an appropriate solvent to remove the products of the reaction. If desired, acidified water can be used to absorb the products of reaction and neutralize unconverted ammonia. The ultimate recovery of the products may be accomplished by conventional means. The efficiency of the scrubbing operation may be improved when water is employed as the scrubbing agent by adding a suitable wetting agent in the water. Where molecular oxygen is employed as the oxidizing agent in this process, the resulting product mixture after the removal of the nitriles may be treated to remove carbon dioxide, with the remainder of the mixture containing the unreacted olefin and oxygen being recycled through the reactor. In the case where air is employed as the oxidizing agent in lieu of molecular oxygen, the residual product after separation of the nitriles and other carbonyl products may be scrubbed with a non-polar solvent, e.g., a hydrocarbon fraction in order to recover unreacted olefin, and in this case the remaining gases may be discarded. The addition of a suitable inhibitor to prevent polymerization of the unsaturated products during the recovery steps is also contemplated.

The catalyst useful in the process of the present invention is a mixture, compound or possibly complex of the oxides of iron, bismuth, molybdenum, nickel and magnesium, at least one or more element selected from potassium and cesium, and optionally one or more elements selected from the group comprising cobalt, manganese, chromium, phosphorous, antimony, tellurium, sodium, cerium and/or tungsten. The composition is characterized by in the following empirical formula:

$$A_a K_b Cs_c Mg_d Ni_e Fe_f Bi_g Mo_{12}O_x$$

wherein A is one or more of the elements selected from the group comprising cobalt, manganese, chromium, phosphorus, antimony, tellurium, sodium, cerium and tungsten wherein (a) is a number from 0 to 5, (b) is a number from 0 to 0.4, (c) is a number from 0 to 0.4, provided that the sum of (b) and (c) is from 0.1 to 0.4, (d), (e), (f), and (g) are a number from about 0.2 to 10, and (x) is a number determined by the valence requirements of the other elements present. Preferably, the sum of (b) and (c) is a number from greater than 0.1 to 0.4. More preferably the sum of (b) and (c) is a number from 0.125–0.3.

The catalyst of this invention may be prepared by any of the numerous methods of catalyst preparation which are known to those skilled in the art. For example, the catalyst may be manufactured by co-precipitating the various ingredients. The co-precipitated mass may then be dried and ground to an appropriate size. Alternately, the co-precipitated material may be slurried and spray-dried in accordance with conventional techniques. The catalyst may be extruded as pellets or formed into spheres in oil as is well-known in the art. Alternatively, the catalyst components may be mixed with the support in the form of the slurry followed by drying, or they may be impregnated on silica or other supports.

A particularly attrition-resistant form of the catalyst may be prepared by adding the support material to the catalyst in two stages, first by preparing and heat-treating a mixture of active catalyst components and from 0 to 60% by weight of the total support material, followed by adding the remainder of the support material to the powdered form of the heat-treated catalyst.

Potassium, cesium, and sodium may be introduced into the catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Preferred are the water-soluble salts which are easily dispersible within the catalyst and which form stable oxides upon heat-treating. An especially preferred source for introducing bismuth is bismuth nitrate which has been dissolved in a dilute solution of $HNO_3$.

To introduce the iron component into the catalyst one may use any compound of iron which, upon calcination, will result in the oxides. As with the other elements, water-soluble salts are preferred for the ease with which they may be uniformly dispersed within the catalyst. Most preferred is ferric nitrate. Cobalt, nickel and magnesium may be similarly introduced. However, magnesium may also be introduced into the catalyst as an insoluble carbonate or hydroxide which upon heat-treating results in an oxide.

To introduce the molybdenum component, any molybdenum oxide such as the dioxide, trioxide, pentoxide, or sesquioxide may be used; more preferred is a hydrolyzable or decomposable molybdenum salt. The most preferred starting material is ammonium heptamolybdate.

Phosphorus may be introduced as an alkali metal salt, an alkaline earth metal salt or the ammonium salt, but is preferably introduced as phosphoric acid.

Other elements may be introduced, starting with the metal, oxidizing the metal with an oxidizing acid such as nitric acid, and then incorporating the nitrate into the catalyst. Generally, however, the nitrates are readily available and form a very convenient starting material.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result in the oxides of the instant catalyst upon heating to a temperature within the range disclosed hereinafter.

The catalyst can be employed without a support and will display excellent activity. The catalyst can also be combined with a support, and preferably it is combined with at least 10 percent up to about 90 percent of the supporting compound by weight of the entire composition. Any known support materials can be used, such as, silica, alumina, zirconia, titania, alundum, silicon carbide, alumina-silica, the inorganic phosphates such as aluminum phosphate, silicates, aluminates, borates, carbonates, and materials such as pumice, montmorillonite, and the like that are stable under the reaction conditions to be encountered in the use of the catalyst. The preferred support is silica, which is added to the slurry during the preparation of the catalyst in the form of silica sol or fumed silica. The level of support is usually in the range of 10-70% weight present. Preferably, the level of support is in the range of 40-60% weight present.

The catalytic activity of the system is enhanced by heating at an elevated temperature. Generally, the catalyst mixture is spray dried at a temperature of between about 110° C. to 350° C. and then heat treated in stages for from about one to twenty-four hours or more at a temperature of from about 260° to about 1000° C., preferably from 300°-400° C. to 550°-700° C.

In general, activation of the catalyst is achieved in less time at higher temperatures. The sufficiency of activation at any given set of conditions is ascertained by a spot test of a sample of the material for catalytic activity. Activation is best carried out in an open chamber, permitting circulation of air or oxygen, so that any oxygen consumed can be replaced.

Further, pre-treatment or activation of the catalyst before use with a reducing agent such as ammonia in the presence of a limited amount of air at a temperature in the range of 260° to 540° C. is also beneficial.

A preferred method of preparing the catalyst of this invention and a more complete description of the process of the invention can be obtained from the following examples. In addition to the production of unsaturated nitriles, the catalyst of this invention is also useful for the conversion of olefins, such as propylene and isobutylene, to the corresponding unsaturated aldehydes and unsaturated carboxylic acids.

EXAMPLES 1 TO 10

The catalysts employed in the examples of this invention were prepared by essentially the same procedure as described herein below, using the appropriate starting materials.

$Fe(NO_3)_3 \cdot 9H_2O$ was dissolved in $H_2O$ on a hot plate. The other nitrates were then added in the following order; $Mn(NO_3)_2$—50%Sol., $Bi(NO_3)_3 \cdot 5H_2O$, $Ni(NO_3)_2 \cdot 6H_2O$, $Mg(NO_3)_2 \cdot 6H_2O$, $KNO_3$—10% Soln., and $CsNO_3$—10% Soln. A dark greenish brown solution was formed which was maintained at approximately 60° C. $(NH_4)_6Mo_7O_{24} \cdot 4H_2O$ was dissolved in $H_2O$, at approximately 60° C. A silica sol (a highly dispersed colloidal silica) was added, followed by addition of $CrO_3$ (which had been dissolved in $H_2O$). Next, the nitrate solution was added to form a greenish yellow slurry, which was then evaporated on a hot plate with constant stirring until thickening occurred. The next step involved drying at about 120° C. Following drying, the catalyst was denitrified by heating at 290° C. for 3 hours, followed by heating at 425° C. for 3 hours, and finally calcining at about 610° C. for 3 hours. Table I shows the starting materials for each example catalyst prepared by the above described procedure.

TABLE I

| STARTING MATERIALS FOR CATALYST FORMATION (Grams) | | | | | | | |
|---|---|---|---|---|---|---|---|
| | $KNO_3$ | $CsNO_3$ | $Ni(NO_3)_2 \cdot 6H_2O$ | $NaNO_3$ | $Mg(NO_3)_2 \cdot 6H_2O$ | $Co(NO_3)_2 \cdot 6H_2O$ | $Fe(NO_3)_3 \cdot 9H_2O$ |
| Example | | | | | | | |
| 1 | *0.61 | *0.88 | 21.81 | — | 7.69 | — | 10.91 |
| 2 | *1.36 | *2.05 | 21.81 | — | 7.69 | — | 10.91 |
| 3 | 0.61 | 0.88 | 21.81 | — | 7.69 | — | 10.91 |
| 4 | *0.30 | *0.29 | 17.45 | — | 9.62 | 2.18 | 12.12 |
| 5 | *2.27 | *1.46 | 17.45 | — | 9.62 | 2.18 | 12.12 |
| 6 | 0.76 | 1.46 | 17.45 | — | 9.62 | 2.18 | 12.12 |
| 7 | *0.45 | — | 21.81 | 0.64 | 7.69 | — | 15.15 |
| 8 | *3.79 | — | 21.81 | 0.64 | 7.69 | — | 15.15 |
| 9 | *3.03 | *0.44 | 21.81 | 0.64 | 7.69 | — | 15.15 |
| 10 | 1.14 | *2.92 | 21.81 | 0.64 | 7.69 | — | 15.15 |
| | $Mn(NO_3)_2$—50% Soln | $Bi(NO_3)_3 \cdot 5H_2O$ | $H_3PO_4$—85% Soln | $WO_3$—85% Soln | $CrO_3$ | $(NH_4)_6Mo_7O_{24}$ | $SiO_2$ Sol —40% |
| Example | | | | | | | |
| 1 | 2.42 | 3.27 | — | — | 0.68 | 31.78 | 93.29 |
| 2 | 2.42 | 3.27 | — | — | 0.68 | 31.78 | 93.59 |
| 3 | 2.42 | 3.27 | — | — | 0.68 | 31.78 | 95.36 |
| 4 | — | 3.64 | — | 2.05 | — | 31.78 | 95.36 |
| 5 | — | 3.64 | — | 2.05 | — | 31.78 | 95.80 |
| 6 | — | 3.64 | — | 2.05 | — | 31.78 | 98.79 |
| 7 | — | 5.46 | 0.86 | — | — | 31.78 | 97.06 |
| 8 | — | 5.46 | 0.86 | — | — | 31.78 | 97.45 |
| 9 | — | 5.46 | 0.86 | — | — | 31.78 | 97.44 |
| 10 | — | 5.46 | 0.86 | — | — | 31.78 | 98.86 |

* = 10% Solution.

In the examples given, percent conversion to the unsaturated nitrile is defined as follows:

Mole percent per pass conversion (PPC) to unsaturated nitrile =

$$\frac{\text{Mols of nitrile product obtained}}{\text{Total Mols of olefin converted to all products}} \times 100$$

Ammoxidation reactions carried out with the catalyst compositions of this invention employing propylene as the hydrocarbon feeds are summarized in Table II. Each reaction was run in a ⅜ inch diameter stainless steel microreactor. A 3.7 gram sample of 20-35 mesh catalyst was employed. The data in these tables show that per pass conversions to acrylonitrile obtained with catalysts of the present invention are substantially higher than those obtained with catalysts of the prior art.

TABLE II

CONVERSION OF PROPYLENE TO ACRYLONITRILE

Fixed - Bed Reactor  
Reaction Temperature: 430° C.  
Contact Time: 6.0 seconds  
Run Time: 30 minutes  
Feed Ratio (Molar) $C_3^=/NH_3/O_2/N_2/H_2O = 1.8/2.2/3.6/2.4/6$

| Example | Catalyst Composition | $C_3^=$Conversion | Acrylonitrile % Yield | Acrylonitrile % Selectivity |
|---|---|---|---|---|
| *1. | 50% $K_{0.04}Cs_{0.03}Ni_5Mg_2Fe_{1.8}Mn_{0.45}Bi_{0.45}Cr_{0.45}Mo_{12}O_x$ + 50% $SiO_2$ | 100.0 | 78.6 | 78.6 |
| *2. | 50% $K_{0.09}Cs_{0.07}Ni_5Mg_2Fe_{1.8}Mn_{0.45}Bi_{0.45}Cr_{0.45}Mo_{12}O_x$ + 50% $SiO_2$ | 98.8 | 84.2 | 85.2 |
| *3. | 50% $K_{0.4}Cs_{0.3}Ni_5Mg_2Fe_{1.8}Mn_{0.45}Bi_{0.45}Cr_{0.45}Mo_{12}O_x$ + 50% $SiO_2$ | 19.4 | 15.2 | 78.5 |
| *4. | 50% $K_{0.02}Cs_{0.01}Ni_4Co_{0.5}Mg_{2.5}Fe_2Bi_{0.5}W_{0.5}Mo_{12}O_x$ + 50% $SiO_2$ | 99.1 | 73.9 | 74.5 |
| 5. | 50% $K_{0.15}Cs_{0.05}Ni_4Co_{0.5}Mg_{2.5}Fe_2Bi_{0.5}W_{0.5}Mo_{12}O_x$ + 50% $SiO_2$ | 94.0 | 80.3 | 85.4 |
| *6. | 50% $K_{0.50}Cs_{0.50}Ni_4Co_{0.5}Mg_{2.5}Fe_2Bi_{0.5}W_{0.5}Mo_{12}O_x$ + 50% $SiO_2$ | 22.7 | 17.0 | 75.0 |
| *7. | 50% $K_{0.03}Na_{0.5}Ni_5Mg_2Fe_{2.5}Bi_{0.75}P_{0.5}Mo_{12}O_x$ + 50% $SiO_2$ | 95.3 | 69.5 | 72.6 |
| 8. | 50% $K_{0.25}Na_{0.5}Ni_5Mg_2Fe_{2.5}Bi_{0.75}P_{0.5}Mo_{12}O_x$ + 50% $SiO_2$ | 95.3 | 72.8 | 76.4 |
| 9. | 50% $K_{0.20}Cs_{0.015}Na_{0.5}Ni_5Mg_2Fe_{2.5}Bi_{0.75}P_{0.5}Mo_{12}O_x$ + 50% $SiO_2$ | 94.9 | 72.8 | 76.7 |
| *10. | 50% $K_{0.75}Cs_{0.1}Na_{0.5}Ni_5Mg_2Fe_{2.5}Bi_{0.75}P_{0.5}Mo_{12}O_x$ + 50% $SiO_2$ | 47.3 | 35.2 | 74.4 |

*Comparative examples

What is claimed:

1. A catalyst composition comprising a complex of the catalytic oxides of iron, bismuth, molybdenum, nickel, magnesium, cesium, potassium, and optionally one or more of cobalt, manganese, chromium, phosphorous, antimony, tellurium, sodium, cerium and/or tungsten and having the formula:

$$A_aK_bCs_cMg_dNi_eFe_fBi_gMo_{12}O_x$$

wherein

A is one or more of Co, Mn, Cr, P, Sb, Te, Na, Ce, or W wherein a is a number from 0 to 5.0;
b is a number from 0.09 to 0.4;
c is a number from 0.015 to 0.4;
provided that the sum of b and c is from 0.1 to 0.4; d, e, f and g are numbers from 0.2 to 10; and x is a number determined by the valence requirements of the other elements present.

2. The catalyst composition of claim 1, wherein said catalyst consists essentially of:

$$A_aK_bCs_cMg_dNi_eFe_fBi_gMo_{12}Ox$$

3. The composition of claim 1 wherein said catalyst consists of:

$$A_aK_bCs_cMg_dNi_eFe_fBi_gMo_{12}Ox$$

4. The composition of claim 1 wherein said catalyst is supported on a catalyst support material selected from the group consisting of silica, alumina or mixtures thereof.

* * * * *